(12) United States Patent
Sekutowski et al.

(10) Patent No.: US 6,464,995 B1
(45) Date of Patent: *Oct. 15, 2002

(54) TREATED HORTICULTURAL SUBSTRATES

(75) Inventors: Dennis G. Sekutowski, Stockton, NJ (US); Gary J. Puterka; David Michael Glenn, both of Shepherdstown, WV (US)

(73) Assignees: Engelhard Corporation, Iselin, NJ (US); The United States of America as represented by the Secretary of Agriculture, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,538

(22) Filed: Apr. 20, 2000

Related U.S. Application Data (63) Continuation of application No. 08/972,648, filed on Nov. 18, 1997, now Pat. No. 6,154,327, which is a continuation-in-part of application No. 08/812,301, filed on Mar. 5, 1997, now Pat. No. 5,908,708.

(51) Int. Cl.$^7$ .......................... A01N 25/04; A01N 25/32
(52) U.S. Cl. ..................... 424/405; 47/2; 47/58.1; 47/DIG. 11; 424/421; 424/DIG. 10; 427/384; 427/393.1; 428/541; 504/362; 516/77; 516/88; 516/104
(58) Field of Search ................ 47/2, 58.1, DIG. 11; 427/384, 393.4; 428/541; 516/79, 88, 104; 424/405, 421, DIG. 10; 504/362

(56) References Cited

U.S. PATENT DOCUMENTS

| | | |
|---|---|---|
| 2,441,423 A | 5/1948 | Elliot et al. |
| 2,733,160 A | 1/1956 | Iler |
| 2,818,340 A | 12/1957 | Goddin et al. |
| 2,948,632 A | 8/1960 | Albert et al. |
| 3,120,445 A | 2/1964 | Aluisi et al. ................ 106/286 |
| 3,124,505 A | 3/1964 | Doyle et al. |
| 3,159,536 A | 12/1964 | Marotta |
| 3,227,657 A | 1/1966 | Haden et al. |
| 3,235,451 A | 2/1966 | Odeneal |
| 3,346,507 A | 10/1967 | Taulli |
| 3,964,649 A | 6/1976 | Alexander ................... 222/399 |
| 4,071,374 A | 1/1978 | Minton ........................ 106/189 |
| 4,098,600 A | 7/1978 | Chupp ........................... 71/105 |
| 4,203,864 A | 5/1980 | Sawyer, Jr. |
| 4,274,883 A | 6/1981 | Lumbeck et al. ........... 106/308 |
| 4,279,895 A | 7/1981 | Carle ........................... 424/127 |
| 4,382,868 A | 5/1983 | House |
| 4,632,936 A | 12/1986 | Boase et al. ................ 514/465 |
| 4,634,463 A | 1/1987 | Ohsuga ........................... 71/34 |
| 4,705,816 A | 11/1987 | Pole et al. ...................... 43/52 |
| 5,122,518 A | 6/1992 | Vrba ............................ 514/63 |
| 5,151,122 A | 9/1992 | Atsumi et al. .......... 424/421 X |
| 5,392,559 A | 2/1995 | Long ............................. 43/52 |
| 5,393,461 A | 2/1995 | Fillipova | 
| 5,414,954 A | 5/1995 | Long ........................... 43/121 |
| 5,455,220 A | 10/1995 | Dedolph ...................... 504/241 |
| 5,480,638 A | 1/1996 | Erwin ......................... 424/614 |
| 5,628,144 A | 5/1997 | Eastin ............................ 47/58 |
| 5,656,571 A | 8/1997 | Miller et al. ................ 504/116 |
| 5,908,708 A | * 6/1999 | Sekutowski et al. ........ 428/541 |
| 6,027,740 A | * 2/2000 | Puterka et al. .............. 424/405 |
| 6,156,327 A | * 12/2000 | Sekutowski et al. ........ 424/405 |

FOREIGN PATENT DOCUMENTS

| | | | |
|---|---|---|---|
| BE | 855480 | 10/1990 | |
| DE | 2005190 A | 9/1970 | |
| DE | 002067948 | 8/1974 | |
| DE | 2926095 | 3/1980 | |
| DE | 4322939 | 1/1995 | |
| DE | 19505382 | 8/1996 | |
| EP | 035432 | 2/1990 | |
| EP | 0367934 | 5/1990 | |
| JP | 0224629 | 12/1984 | ..................... 47/2 |
| SU | 17922573 A | 6/1990 | |
| WO | WO94/09626 | 5/1994 | |

OTHER PUBLICATIONS

Section Ch, week 8403, Derwent Publications Ltd., London, GB, Class A97, An 84–014859, XP002069730 "Hydrophobic Silicic Acid Produce React Alkali Metal Silicate Mineral Acid Treat Product Silicone Oil" Nippon Silica Kogyo KK.

D.M. Glenn, et al. "Hydrophobic Particles For Pest Control in Deciduous Tree Fruit Production" XP002069729. Hortscience, vol. 32, No. 3, 1997, p. 467.

Section CH, week 7421, Derwent Publications Ltd., London, GB, Class A82, AN 74–38844V, XP002069731 "Water Repellent Coatings Based on Silica Fine Powder Paper Wood Concrete Mortar Gypsum Substrate", S. Shimoda.

Driggers, B. F. "Experiments with Talc and Other Dusts Used Against Recently Hatch Larvae of the Oriental and Codling Moths," J. Econ, Ent., 22 327–334 (1929).

Hunt, C.R., "Toxicity of Insecticide Dust Diluents and Carriers to Larvae of the Mexican Bean Beetle," J. Econ. Ent., 40 215–219 (1947).

P. Alexander, J.A. Kitchener and H.V.A. Briscoe, "Inert Dust Insecticides," Parts I, II, and III, Ann. Appl. Biol., 31 143–159 (1944).

W. Ebeling, R. F. Wagner "Rapid Desiccation of Drywood Termites with Inert Sorptive Dusts and Other Substances," J. Econ. Ent., 52 190–207 (1959).

M. Bar–Joseph, H. Frenkel "Spraying Citrus Plants with Kaolin Suspensions Reduces Colonization by The Spiraea Aphid," Crop Prot 2 371–374 (1983).

J.S. Dhaliwal, "Effect of Rainfall and Kaolinite Spray on the Corn Aphid, Rhopalosiphum Maidis (Fitch) Infesting Barley (Hordeim Vulgare Linn)," Forage Res. 5:155–157 (1979).

(List continued on next page.)

Primary Examiner—Richard D. Lovering
(74) Attorney, Agent, or Firm—Raymond F. Keller (57) ABSTRACT

Disclosed are horticultural substrates coated with a particulate membrane and a method for controlling pests and providing enhanced horticultural effect by applying a particulate membrane to the surface of the horticultural substrate.

39 Claims, 6 Drawing Sheets

OTHER PUBLICATIONS

A. Boyce, "Mortality of Rhagoletis Completa Cress. (Diptera:Trypetidae) Through Ingestion of Certain Solid Materials," J. Econ. Ent., 25 1053–1059 (1932).

C. Richardson L. Glover, "Some Effects of Certain 'Inert' and Toxic Substances Upon the Twelve–Spotted Cucumber Beetle, Diabrotica Duodecimpunctata," J. Econ. Ent., 25 1176–1181 (1932).

A. Farmer, "The Effects of Dust on Vegetation: A Review," Envir Pol 79 (1193) 63–75.

V. Wigglesworth, "Action of Inert Dusts on Insects," Nature 153 (1944) 493–494.

W. David, B. Gardiner, "Factors Influencing the Action of Dust Insecticides," Bul Ent. Res. (1950) 41 1–61.

H. Kalmus, "Action of Inert Dusts on Insects," Nature 33 (1945) 188–189.

J. Kring, "Flight Behavior of Aphids," Ann Rev Ent. 17 461–493 (1972).

S. Chiu, Toxicity Studies of So–Called 'Inert' Materials with the Bean Weevil, Acanthoscelides Obtectus (Say) J. Econ. Ent. 32 240–248 (1939).

M. Baradas, B. Blad, N. Rosenberg, "Reflectant Induced Modification of Soybean Canopy Radiation Balance v. Longwave Radiation Balance," Agron J. 68 848–852 (1976).

G. Stanhill, S. Moreshet, M. Fuchs, "Effect of Increasing Foliage and Soil Reflectivity on the Yield and Water use Efficiency of Grain Sorghum," Agron J. 68 329–332 (1976).

S. Moreshet, S. Cohen, Y. Fuchs, "Effect of Increasing Foliage Reflectance on Yield, Growth and Physiological Behavior of a Dryland Cotton Crop," Crop Sci 19 863–868 (1979).

R. Yokomi, "A Preliminary Report of Reduced Infection by Spiroplasma Citri and Virescence in Whitewash–Treated Periwinkle," Phytopathology 71 914 (1981).

D. Eveling, "Similar Effects of Suspensions of Copper Oxychloride and Kaolin on Sprayed Leaves," Ann Apply Biol. (1972) 70, 245–249.

J. Jack, J. Gilbert, "The Effect of Suspended Clay on Ciliate Population Growth Rates," Freshwater Biol. (1993) 29, 385–394.

H. Uppal, S. Cheema, "Effect of Mulches and Kaolin Spray on Soil Temperature, Growth, Yield and Water Use of Barley," Ind J. Agric Sci (1981) 51, 653–659.

D. Meador, "Reducing Russet on 'Golden Delicious' Apples with Silicon Dioxide Formulation Foliage Sprays," Hort Sci (1977) 12, 504–505.

T. Babu, S. Hussaini, B. Satyanarayana, "Effect of Pre–Storage Seed Treatements on Adult Mortality, Oviposition and Development of Callosobruchus Chinensis L. (Bruchidae-:Coleoptera) and the Viability of Mungbean (Vigan Radiata (L.) Wilczek) in India," Tropical Pest Mgt (1989) 35, 397–398.

R. Campbell, J. Ephgrave, "Effect of Bentonite Clay on the Growth of Gaeumannomyces Graminis var. tritici and on Its Interactions with Antagonistic Bacteria," J Gen Microbiol (1983) 129, 771–777.

J. Desmarchelier, C. Ahern, "Insecticide–Rententive Carriers 2. Fenitrothion–Impregnated Clays," Aus J Exper Agric (1988) 28, 271–8.

R. Wagner, W. Ebeling, "Lethality of Inert Dust Materials to Kalotermes Minor Hagen and Their Role as Preventivesin Structural Pest Control," J. Econ. Ent., (1959) 52, 208–212.

J.S. Kennedy, C.O. Booth, W.J.S. Kershaw, "Host Finding by Aphids In the Field," Ann Appl. Biol (1961), 49, 1–21.

W.O. Cline, R.D. Millholland, "Root Dip Treatments for Controlling Blueberry Stem Blight Caused by Botryosphaeria Dothidea in Container–Grown Nursery Plants," Plant Disease 76, 136–138 (1992).

J. Norman, "Development of Colletotrichum Gloesporioides f. sp. Clidemiae and *Septoria passiflorae* into Two Mycroherbicides with Extended Viability," Plant Disease 79, 1029–1032 (1995).

S. K. Bhattacharyya, M. K. Basu, "Kaoline Powder as a Fungal Carrier," Appl. Envir. Microbiol. 44, 751–753 (1982).

R. H. Daines, R.J. Lukens, E. Brennan, I. Leone, "Phytotoxicity of Captan as Influenced by Formulation, Environment and Plant Factors," Phytopathology (1957) 47, 567–572.

RDF Young, JRM Thacker, DJ Curtis, "The Effects of Three Adjuvants On the Retention of Insecticide Formulations by Cabbage Leaves,"J. Environ. Sci. Health (1996) B31, 165–178.

G. Haukenes, BK Hjeltns, "Kinetics of the Binding of Immunoglobulins, Antibodies and Virus Haemagglutination Inhibitors to Kaolin," Biologicals (1991) 19, 31–35.

J. Han, "Use of Antitranspirant Epidermal Coatings for Plant Protection in China," Plant Dis. (1990) 74, 263–266.

O. Ziv, RA Frederiksen, "The Effect of Film–Forming Anti–Transpirants on Leaf Rust and Powdery Mildew Incidence on Wheat," Plant Path (1987) 36, 242–245.

C. Jacob, et al. "New Strategies in the Control of Major Leaf Disease of Hevea," J. Myco & Plant Path (1195) 25, 120.

S. Marco, "Incidence of Nonpersistently Transmitted Viruses in Pepper Sprayed with Whitewash, Oil, and Insecticide, Alone or Combined," (1993) Plant Dis 77, 1119–1122.

Ziv, O. "Control of Septoria Leaf Blotch of Wheat and Powdery Mildew of Barley with Antitranspirant Epidermal Coating Materials," Phytopar (1983) 11, 33–38.

M. Kamp, "Control of Erysiphe Cichoracearum on Zinnia Elegans, with a Polymer–Based Antitranspirant," Hort Sci (1985) 20, 879–881.

J. Zekaria–Oren, Z Eyal, "Effect of Film–Forming Compounds on the Development of Leaf Rust on Wheat Seedlings," Plant Dis (1991) 75, 231–234.

A. Franck, M. Bar–Joseph, "Use of Netting and Whitewash Spray to Protect Papaya Plants Against Nivun Haamir (NH) Dieback Disease," Crop Prot (1992) 11, 525–528.

O. Ziv, "Effects of Bicarbonates and Film–Forming Polymers on Cucurbits Foliar Diseases," Plant Dis (1992) 76, 513–517.

TC Helvey, "Insecticidal effect of Inert Solid Diluents," Sci (1952) 116, 631–632.

HG Guy, HF Dietz "Further Investigations with Japanese Beetle Repellants," J. Econ. Ent., (1939) 32, 248–252.

C. Conceicao, A. Mexia, A. Barbosa, "Combined Effects of Silica Aerogels and Insect Growth Regulators Against Sitophilus Zeamais Motch Infestations," Int Cong Ent pro 1996.

MRGK Nair, "Structure of Waterproofing Epicuticular Layers in Insects in Relation to Inert Dust Action" Indian J. Ent. (1957) 19, 37–49.

BR Bartlett, "The Action of Certain 'Inert' Dust Materials on Parasitic Hymenoptera," J. Econ. Ent. (1951) 44, 891–896.

GL Hockenyos, "The Effect of Dusts on the Oriental Roach," J. Econ. Ent. (1933) 26, 792–794.

T. Hirano, M. Kiyota, I. Aiga, "Physical Effects of Dust on Leaf Physiology of Cucumber and Kidney Bean Plants," Envirn Poll (1995) 89, 255–261.

NKS Rao, "The Effects of Antitranspirants on Leaf Water Status, Stomatal Resistance and Yield in Tomato," J Hort Sci (1985) 60, 89–92.

DW Eveling MZ Eisa, "The Effects of a Cuticle–Damaging Kaolin On Herbicidal Phytoxicity," Weed Res (1976) 16, 15–18.

S. Marco, O. Ziv, R. Cohen, "Suppression of Powdery Mildew in Squash by Applications of Whitewash, Clay and Anitranspirant Materials," Phytopar (1194) 22, 19–29.

SM Lipson, G. Stotzky, "Effect of Kaolinite on the Specific Infectivity of Reovirus," FEMS Micr. Let. 37, 83–88 (1986).

S. Lavie, G. Storzky, "Adhesion of the Clay Minerals Montmorillonite, Kaolinite, and Attapulgite reduces Respiration of Histoplasma Capsulatum," App & Envir Micro (1986) 51, 65–73.

MS Rajan, KR Reddy, RS Rao, GHS Reddi, "Effect of Antitranspirants and Reflectants on Pod Yield of Rainfeld Groundnut," Agri Sci Dig (1981) 1, 205–206.

W. Ebeling, RJ Pence, "Termites and Other Enemies of Wood," Pest Cont. Oct. 1956, 46–64.

DW Eveling, A. Bataille, "The Effect of Deposits of Small Particles on the Restisance of Leaves and Petals to Water Loss," Envirn Poll (1984) 36, 229–238.

M. Llewellyn, J. Ervaz, "Abrasive Dusts as a Mechanism for Aphid Control," Ent. Exp. & Appl. 26 (1979) 219–222.

M. Swamiappan, S. Jayaraj, KC Chandy, "Effect of Activated Kaolinitic Clay on Some Storage Insects," Z. Ang. Ent. 80 (1976), 385–389.

D Permual, G. Le Patourel, Laboratory Evaluation of Acid–Activated Kaolin to Protect Stored Paddy Against Infestation by Stored Product Insects, J. Stored Prod. Res. 26, 149–153, 1990.

D Permual, G Le Patourel, "Small Bin Trials to Determine the Effectiveness of Acid–Activated Kaolin Against Four Species of Beetles Infesting Paddy Under Tropical Storage Conditions," J. Stored Prod. Res. 28, 193–199 (1992).

DT Lowery, MK Sears, CS Harmer, "Control of Turnip Mosaic Virus of Rutabaga With Applications of Oil, Whitewash, and Insecticides," J. Econ. Ent. (1990) 83, 2352–2356.

S. Marco, "Incidence of Aphid–Transmitted Virus Infections Reduced by Whitewash Sprays on Plants," Amer, Phytop (1986) 76, 1344–1348.

J. Basnizki, M. Evenari, "The Influence of a Reflectant on Leaf Temperature and Development of the Glove Artichoke (*Cynara scolymus* L.)," J. Am Soc Hort Sci 100, 109–112 (1975).

EF Durner, TJ Gianfagna, "Interactions of Ethephon, Whitewashing, and Dormant Oil on Peach Pistil Growth, Hardiness and Yield," Am Hort Sci 27, 104–105 (1992).

EF Durner, TJ Gianfagna, "Peach Pistil Growth Inhibition and Subsequent Bloom Delay by Midwinter Bud Whitewashing," Am Hort Sci 25, 1222–1224 (1990).

WJ Lipton, "Temperatures and Net Heat Gain in Normal and Whitewashed Cantaloupe Fruits," J. Amer. Hort. Sci. 97, 242–244 (1972).

WJ Lipton, F. Matoba, "Whitewashing to Prevent Sunburn of 'Crenshaw' Melons," Hortscience, 6, 343–345 (1971).

WS Cranshaw, DJ Liewehr, "Effects of Colored Sprays on Aphid & Dsyllid Colonization," SW Entomol 15, 205–209 (1990).

S. Marco, "Possible Modes of Action of Whitewash in Reducing Virus Incidence in Potatoes," Potato Res 33, 138–129 (1990).

I. Bar–Zakay, M. Gokkes, Y. Oren, "Chemical Control of Aphids on Citrus Bearing Trees," Phytoparasitica 15, 343 (1987).

S. Marco, "Reducing the Incidence of Aphid–Transmitted Viruses by Reflective Materials," Phytoparasitica 13, 279–280 (1985).

DJ Gumpf, GN Oldfield, RK Yokomi, "Progress in the Control of Citrus Stubborn Disease," Proc Int. Soc. Citric, 457–458 (1981).

JGM Vos, TS Uhan, B. Sutarya, "Intergrated Crop Management of Hot Peppers," Crop Prot. 14, 445–452 (1995).

CG Summers, JJ Stapleton, AS Duncan, DA Hart, "Comparison of Sprayable and Film Mulches in Delaying the Onset of Aphic–Transmitted Virus Diseases in Zucchini Squash," Plant Dis (1995) 79, 1126–1131.

PC Nicot, M. Mermier, BE Vaissiere, J. Lagier, "Differential Spore Production for Botrytis Cinerea on Agar Medium and Plant Tissue Under Near–Ultraviolet Light–Absorbing Polyethylene Film" Plant Dis (1196) 80, 555–558.

JJ Stapleton, WK Asai, JE DeVay, "Use of Polymer Mulches in Intergrated Pest Management Programs for Establishment of Perennial Fruit Crops," (1989) Acta Hort. 255, 161–168.

RE Byers, CG Lyons, "Effect of Chemical Deposits from Spraying Adjacent Rows on Efficacy of Peach Bloom Thinners," HortSci (1985) 20, 1076–1078.

RE Byers, KS Yoder, GE Mattus, "Reduction in Russetting of 'Golden Delicious' Apples with 2, 4, 5–TP and Other Compounds," HortScience 18:63–65 (1983).

RE Byers, DH Carbaugh, CN Presley, "'Stayman' Fruit Cracking as Affected by Surfactants, Plant Growth Regulators, and Other Chemicals," J. Amer. Soc. Hort. Sci. 155:405–411 (1990).

Database WPI, Section Ch, Week 9411, Derwent Publications Ltd., London, GB; "Insection Pest Control by Dispersing Insecticidal Solid Particles having Smaller Size than Distance Between Hairs on Insects, with Dispersion Apparatus," Shikoku Sogo Kenkyusho.

Chemical Abstracts, vol. 122, No. 9, Feb. 27, 1995, Columbus, Ohio, U.S. "Insecticides in the Solid Form," Yamamoto, Naoaki, JP (Shikoku).

Chemical Abstracts, vol. 103, No. 23, Dec. 9, 1985, Columbus, Ohio, U.S., Tomono Noyaku K.K., Japan "Tea " thrip Repellents.

Chemical Abstracts, vol. 114, No. 5, Feb. 4, 1991, Columbus, Ohio, U.S., Hung, T., "Prevention of Apple Russet With Aqueous Mineral Suspension Sprays," Mar. 28, 1990.

* cited by examiner

TREATED HORTICULTURAL SUBSTRATES

This application is a continuation of U.S. patent application Ser. No. 08/972,648, filed Nov. 18, 1997 now U.S. Pat. No. 6,156,327, which is a continuation-in-part of U.S. patent application Ser. No. 08/812,301, filed Mar. 5, 1997 now U.S. Pat. No. 5,908,708.

FIELD OF THE INVENTION

The present invention is directed to horticultural substrates treated with a particulate membrane and methods for controlling pests associated with such substrates and for providing enhanced horticultural effects.

BACKGROUND OF THE INVENTION

The prior art has discussed the use of certain inert particulate solids as insecticides, see for example; Driggers, B. F., "Experiments with Talc and Other Dusts Used Against Recently Hatched Larvae of the Oriental and Codling Moths," *J. Econ. Ent.,* 22 327–334 (1929); Hunt, C. R., "Toxicity of Insecticide Dust Diluents and Carriers to Larvae of the Mexican Bean Beetle," *J. Econ. Ent.,* 40 215–219 (1947); P. Alexander, J. A. Kitchener and H. V. A. Briscoe, "Inert Dust Insecticides," Parts I, II, and III, *Ann. Appl. Biol.,* 31 143–159, (1944); and U.S. Pat. No. 3,159,536 (1964) and U.S. Pat. No. 5,122,518 (1992), each of which is incorporated herein by reference with regard to its teachings relating to particulate materials.

Plant diseases are caused by various pathogens, e.g., fungi, bacteria and virus, and these diseases have generally been controlled commercially by the use of chemical pesticides. For example, commercial fungicides generally belong to the following types of chemical compounds: inorganic (copper or sulfur based), organic (anilines, anilides, dithiocarbamates, halogen compounds and heterocyclic nitrogen compounds), antibiotics and biologicals. Chemically toxic fungicides and bactericides are often formulated with inert particulates. Inert particulates, however, have been shown to be ineffective toward these plant pests when applied by themselves (see W. O. Cline and R. D. Milholland, "Root Dip Treatments for Controlling Blueberry Stem Blight Caused by *Botryosphaeria dothidea* in Container-Grown Nursery Plants," *Plant Disease* 76 136–138 (1992)). Furthermore, not only have inert particulates been shown to be ineffective in plant disease control, but it has been reported by S. K. Bhattacharyya and M. K. Basu, "Kaolin Powder as a Fungal Carrier," *Appl. Envir. Microbic.* 44 751–753 (1982) that kaolin powder may be used to carry and preserve an Aspergillus sp. for at least 90 days. In another report, S. M. Lipson and G. Stotzky, "Effect of Kaolinite on the Specific Infectivity of Reovirus," *FEMS Micr. Let.* 37 83–88 (1986), it was reported that the infectivity of enteric viruses (e.g., poliovirus, rotavirus and reovirus) is prolonged when these viruses are adsorbed on naturally occurring particulates (sediments, clay materials) in terrestrial and aquatic environments.

O. Ziv and R. A. Frederiksen, "The Effect of Film-forming Anti-transpirants on Leaf Rust and Powdery Mildew Incidence on Wheat," *Plant Path.* 36 242–245 (1987); M. Kamp, "Control of *Erysiphe cichoracearum* on *Zinnia elegans,* with a Polymer-based Antitranspirant," *Hort. Sci.* 20 879–881 (1985); and J. Zekaria-Oren and Z. Eyal, "Effect of Film-forming Compounds on the Development of Leaf Rust on Wheat Seedlings," *Plant Dis.* 75 231–234 (1991)) discuss the use of anti-transpirant polymer films to control disease. Of course, the use of anti-transpirants is undesirable because they reduce the exchange of necessary gases on the surface of living plants.

For prior art regarding horticultural effects see, for example, Byers, R. E., K. S. Yoder, and G. E. Mattus, "Reduction in Russetting of 'Golden Delicious' Apples with 2,4,5-TP and Other Compounds," *HortScience* 18:63–65); Byers, R. E., D. H. Carbaugh, and C. N. Presley, "'Stayman' Fruit Cracking as Affected by Surfactants, Plant Growth Regulators, and Other Chemicals," *J. Amer. Soc. Hort. Sci.* 115:405–411 (1990); Durner, E. F., and T. J. Gianfagna, "Peach Pistil Growth Inhibition and Subsequent Bloom Delay by Midwinter Bud Whitewashing," *HortScience* 25:1222–1224 (1990); and M. N. Westwood, *Temperate-zone Pomology,* page 313 W. H. Freeman and Co. (1978).

Therefore, there is still a need for cost effective inert, nontoxic improved agents for pest control and for enhanced horticultural effects and methods for their use.

SUMMARY OF THE INVENTION

This invention relates to horticultural substrates where the surface of said substrates is coated with a particulate membrane and to methods for pest control and enhanced horticultural effects by forming said membrane on the surface of the horticultural substrate.

In one embodiment, this invention relates to coated substrates comprising a horticultural substrate wherein the surface of said substrate is coated with a membrane comprising one or more particulate layers, said layers comprising one or more particulate materials, said particulate materials being finely divided, and wherein said membrane allows for the exchange of gases on the surface of said substrate.

In another embodiment, this invention relates to a method for pest control on horticultural substrates which comprises forming on the surface of said substrate a membrane comprising one or more particulate layers, said layers comprising one or more particulate materials, said particulate materials being finely divided, and wherein said membrane allows for the exchange of gases on the surface of said substrate.

In still another embodiment, this invention relates to a method for providing enhanced horticultural effects which comprises forming on the surface of a horticultural substrate a membrane comprising one or more particulate layers, said layers comprising one or more particulate materials, said particulate materials being finely divided, and wherein said membrane allows for the exchange of gases on the surface of said substrate.

DETAILED DESCRIPTION OF THE INVENTION

The horticultural substrates to which this invention relates are agricultural and ornamental crops, including those selected from the group consisting of fruits, vegetables, trees, flowers, grasses, seeds, roots, and landscape and ornamental plants.

The membranes of this invention comprise one or more particulate layers, said layers comprising one or more particulate materials, said particulate materials being finely divided.

The finely divided particulate materials which make up the particulate membrane of this invention may be hydrophilic or hydrophobic materials and the hydrophobic materials may be hydrophobic in and of themselves, e.g., mineral talc, graphite, and Teflon® or may be hydrophilic materials that are rendered hydrophobic by application of an outer coating of a suitable hydrophobic wetting agent (e.g., the particulate material has a hydrophilic core and a hydrophobic outer surface).

Typical particulate hydrophilic materials useful for the purposes of this invention include: minerals, such as calcium carbonate, talc, kaolin (both hydrous and calcined kaolins, with calcined kaolins being preferred), bentonites, clays, attapulgite, pyrophyllite, wollastonite, silica, feldspar, sand, quartz, chalk, limestone, precipitated calcium carbonate, diatomaceous earth and barytes; functional fillers such as microspheres (ceramic, glass and organic), aluminum trihydrate, pyrogenic silica, ceramic fibers and glass fibers; and pigments such as colorants or titanium dioxide.

The surfaces of such materials can be made hydrophobic by addition of hydrophobic wetting agents. Many industrial mineral applications, especially in organic systems such as plastic composites, films, organic coatings or rubbers, are dependent upon just such surface treatments to render the mineral surface hydrophobic; see, for example, Jesse Edenbaum, *Plastics Additives and Modifiers Handbook,* Van Nostrand Reinhold, New York, 1992, pages 497–500 which is incorporated herein by reference for teachings of such surface treatment materials and their application. So-called coupling agents such as fatty acids and silanes are commonly used to surface treat solid particles as fillers or additives targeted to these industries. Such hydrophobic agents are well known in the art and common examples include: chrome complexes such as Volvan® and Quilon® obtained from DuPont; organic titanates such as Tilcom® obtained from Tioxide Chemicals; organic zirconate or aluminate coupling agents obtained from Kenrich Petrochemical, Inc.; organofunctional silanes such as Silquest® products obtained from Witco or Prosil® products obtained from PCR; modified silicone fluids such as the DM-Fluids obtained from Shin Etsu; and fatty acids such as Hystrene® or Industrene® products obtained from Witco Corporation or Emersol® products obtained from Henkel Corporation (stearic acid and stearate salts are particularly effective fatty acids and salts thereof for rendering a particle surface hydrophobic).

Examples of preferred particulate materials suitable for the purposes of this invention that are commercially available from Engelhard Corporation, Iselin, N.J. are the siloxane treated calcined kaolins sold under the trademark Translink®, and stearic acid treated ground calcium carbonates commercially available from English China Clay under the trademarks Supercoat® and Kotamite®.

The term "finely divided" when utilized herein means that the particulate materials have a median individual particle size below about 10 microns and preferably below about 3 microns and more preferably the median particle size is about one micron or less. Particle size and particle size distribution as used herein are measured with a Micromeritics Sedigraph 5100 Particle Size Analyzer. Measurements were recorded in deionized water or hydrophilic particles. Dispersions were prepared by weighing 4 grams of dry sample into a plastic beaker adding dispersant and diluting to the 80 ml mark with deionized water. The slurries were then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph , e.g., 2.58 g/ml for kaolin. The sample cells are filled with the sample slurries and the X-rays are recorded and converted to particle size distribution curves by the Stokes equation. The median particle size is determined at the 50% level.

Preferably, the particulate material has a particle size distribution wherein up to 90% by weight of the particles have a particle size of under about 10 microns, preferably below about 3 microns and more preferably about one micron or less.

The particulate materials particularly suitable for use in this invention are inert, nontoxic and hydrophobic.

As used herein "inert" particulate materials are particles that are not physiological poisons, that is, the particulate materials of this invention do not, as their primary function, kill pests. While not being bound by theory, it is believed that the pest control of this invention is achieved primarily by prophylactic means rather than primarily through the destruction of the unwanted pests.

The particulate materials are preferably nontoxic meaning that in the limited quantities needed for effective pest control or enhanced horticultural effect such materials are not considered harmful to horticultural substrate, animals, the environment, the applicator and the ultimate consumer.

The preferred particulate materials of the instant invention are hydrophobic. Hydrophobicity refers to the physical property of a surface to dislike or repel water. Most mineral particle surfaces are hydrophilic, i.e., water liking. The terms hydrophobic and hydrophilic are. not always accurately used in the literature and both are often confused with similar terms such as, lipophilic or lipophobic, oleophilic or oleophobic, lyophilic or lyophobic, and polar or nonpolar. Hydrophobicity can be described in more quantitative terms by using contact angle measurements. The contact angle is defined by the equilibrium forces that occur when a liquid sessile drop is placed on a smooth surface. The tangent to the surface of the convex liquid drop at the point of contact among the three phases, solid (S), liquid (L) and vapor (V) is the contact angle $\Theta$.

The relationship between the surface tension of the solid-vapor ($\gamma_{SV}$), liquid-vapor ($\gamma_{LV}$) and solid-liquid ($\gamma_{SL}$) can be defined by the following Young's equation:

$$F = \gamma p \cos \theta$$

where F=wetting force; $\gamma$=liquid surface tension; and p=wetting perimeter.

If the water droplet spreads out on the surface the contact angle is less than 90 degrees and the surface is hydrophilic. If the surface is hydrophobic then the contact angle is greater than 90 degrees. Thus, 180 degrees is the maximum hydrophobicity that a surface can have.

Many surfaces change their surface energy upon contact with water (see J. Domingue, Amer. Lab, October 1990). Dynamic contact angle measurements provide both an advancing and receding contact angle. The advancing contact angle is a measurement of the surface hydrophobicity upon initial contact with a liquid, while the receding contact angle measures the hydrophobicity after the surface has been wetted with a liquid. Thus, for the purposes of this invention, "hydrophobic" or "hydrophobicity," when used in reference to the particulate materials useful for the purposes of this invention, such particles may have either an advancing and/or receding contact angle of greater than 90°. Preferred materials have receding contact angles of greater than 90°.

The dynamic contact angles referred to herein are based on a gravimetric principle of the Wilhelmy plate technique and are determined by measurement on the Dynamic Contact Angle Instrument which can measure both advancing and receding contact angles of powdered samples. A dynamic contact angle analysis system (model DCA 315) from ATI Cahn Instruments Inc. was used for all contact angle measurements referred to and reported herein. The surface tension (γ) of deionized water was determined with a standard platinum calibration plate. Powder samples were deposited on dual sided adhesive tape. The perimeter (p) of the tape was determined with a caliper. The impregnated tape was placed in the DCA 315 and lowered and raised in the deionized water at a rate of 159 microns/second for two immersion cycles. The contact angles were determined from the advancing and receding wetting hysteresis curves of the first immersion cycle. Most samples were prepared and run in duplicate and the results averaged. The data analysis was made with a WinDCA software for Windows diagnostic package from the manufacturer, ATI CahR Instruments Inc.

Representative contact angle values for a variety of inert particulate materials are given in Table I. Although many of the powders listed are hydrophilic and have advancing and receding contact angles less than 90°, some hydrophobic particles as measured by the advancing contact angle, for example talc, become hydrophilic upon wetting.

TABLE I

Contact Angle Values of Powders

| Particle | Advancing Contact Angle (°) | Receding Contact Angle (°) |
| --- | --- | --- |
| Calcium Carbonate[1] | 28.4 | 32.5 |
| Calcium Carbonate[2] | 37.8 | 38.1 |
| Calcium Carbonate[3] (ST) | 180 | 171.1 |
| Barytes[4] | 32.2 | 30.3 |
| Mica[5] | 42.3 | 39.9 |
| Mica[6] | 31.5 | 25.0 |
| Silica[7] | 38.5 | 38.2 |
| Diatomite[8] | 39.4 | 35.3 |
| ATH[9] | 38.7 | 0 |
| Wollastonite[10] | 23.1 | 27.5 |
| Wollastonite[11] | 9.4 | 14.1 |
| Talc[12] | 180 | 12.8 |
| Talc[13] | 159.2 | 11.5 |
| Feldspar[14] | 35.9 | 39.2 |
| Nepheline Syenite[15] | 19.4 | 25.4 |
| Kaolin hydrous[16] | 29 | 30.1 |
| Kaolin calcined[17] | 26 | 20.5 |

ST = Surface Treated
[1]Atomite ® (ECC Int.) [2]GS 6532 (Georgia Marble) [3]Kotamite ® (ECC Int.) [4]Bartex ® 65 (Hitox) [5]WG 325 (KMG Minerals) [6]C-3000 (KMG Minerals) [7]Novacite ® L-207A (Malvern Min Co.) [8]Diafil ® 340 (CR Mineral Corp.) [9]Alcan ® SF (Alcan Chemicals) [10]NYAD ® 1250 (NYCO) [11]Wollastokup ® (NYAD) [12]Vantalc ® 6H (RT Vanderbilt)

TABLE I-continued

Contact Angle Values of Powders

| Particle | Advancing Contact Angle (°) | Receding Contact Angle (°) |
| --- | --- | --- |

[13]Vertal ® 710 (Luzenac Amer Inc.) [14]Minspar ® 4 (K-T Feldspar Corp) [15]Minex ® 10 (Unimin) [16]ASP ® 900 (Engelhard Corp) [17]Satintone ® W (Engelhard Corp)

Hydrophilic surfaces can be made hydrophobic by addition of hydrophobic wetting agents as shown in Table II for hydrous and calcined kaolin. However, not all hydrophobic surface treatments render hydrophobicity to a particle as shown in Table II.

TABLE II

Surface Treated Kaolin Particles

| Surface Treatment (1%) | Hydrous Kaolin Advancing Angle (°) | Hydrous Kaolin Receding Angle (°) | Calcined Kaolin Advancing Angle (°) | Calcined Kaolin Receding Angle (°) |
| --- | --- | --- | --- | --- |
| no treatment | 31 | 30 | 26 | 21 |
| Stearic acid[1] | 155.5 | 0 | 166 | 102 |
| Octyltriethoxysilane[2] | 158 | 0 | 180 | 180 |
| Vinyltriethoxysilane[3] | 120 | 22 | 164 | 140 |
| polydimethylsiloxane[4] linear | 27 | 26 | 24 | 26 |
| methylethoxysiloxane polymer[5] | 89 | 24 | 180 | 154 |
| polydimethyl siloxane cyclic[6] | 112 | 45 | 155 | 154 |

[1]Industrene 7018 (Witco) [2]A-137 (Witco) [3]A-151 (Witco) [4]L-45 (Witco) [5]A-272 (Witco) [6]CG-4491 (HULS America Inc.)

The preferred hydrophilic core particles are those, which when treated with a hydrophobic wetting agent and are applied to the surface of a horticultural substrate, form a membrane on the substrate. Examples of such particles are calcium carbonate and kaolin. Calcined kaolin is preferred to hydrous kaolin.

As previously discussed, this invention relates to horticultural substrates wherein the surface of said substrate is coated with a membrane comprising one or more particulate layers. This membrane allows for the exchange of gases on the surface of said substrate. The gases which pass through the membrane are those which are typically exchanged through the surface skin of living plants. Such gases typically include water vapor, carbon dioxide, oxygen, nitrogen and volatile organics.

The portion of a substrate to be covered with said membrane is within the skill of the ordinary artesian. Optimally, the substrate is fully covered with said membrane, and although diminished disease control and/or horticultural effects may result, less than full substrate coverage is within the scope of this invention; preferably, however, the substrate is substantially covered. Reference is made to U.S. Ser. No. 08/972,659, filed concurrently herewith on Nov. 18, 1997, entitled "Method for Providing Enhanced Photosynthesis" now U.S. Pat. No. 6,110,867 and to U.S. Ser. No. 08/972,653 filed concurrently herewith on Nov. 18, 1997, entitled "Method for Protecting Surfaces from Arthropod Infestation" now U.S. Pat. No. 6,027,740 which are incorporated herein by reference for their teachings regarding methods for insect control and improved photosynthesis. Preferably, the membranes of this invention are sufficiently continuous so as to provide effective control of disease. The membrane may have imperfections such as gaps or voids, but such imperfections should not be so large as to materially affect the disease control of such membrane. Such gaps or voids typically will not exceed about 5μ, and are preferably less than 1μ. In another preferred embodiment, the membrane is water repellent. The membrane may be formed by applying one or more layers of finely divided particulate material until a membrane is formed of sufficient thickness and continuity to be an effective disease control barrier, i.e., the particles on the surface of the substrate are so closely associated that pathogens are unable to penetrate the particulate coating and infect the underlying horticultural substrate. For example, this can typically be accomplished by applying in a uniform manner from about 25 up to about 3000 micrograms of particulate material/cm$^2$ of substrate for particles having specific density of around 2–3 g/cm$^3$. In addition, environmental conditions such as wind and rain may reduce coverage of the membrane and, therefore, it is within the scope of this invention to apply the particles one or more times during the growing season of said horticultural crop so as to maintain the desired effect of invention.

This particulate membrane may be prepared by applying a slurry of finely divided particles in a volatile liquid such as water, a low boiling organic solvent or low boiling organic solvent/water mixture. One or more layers of this slurry can be sprayed or otherwise applied to the substrate. The volatile liquid is preferably allowed to evaporate between coatings. Surfactants or dispersants may be useful in preparing an aqueous slurry of the particulate materials of this invention. The membrane of this invention may be hydrophilic or hydrophobic, but is preferably hydrophobic. Normal dusting of particles, aside from not being commercially practical on a large scale due to drift and inhalation hazards, is not effective at forming a membrane on a horticultural substrate suitable for disease control. The membrane of this invention may be formed, however, by carefully applying the finely divided particles to the substrate, e.g., with a paint brush. While not being bound by theory, it is believed that the one or more layers of finely divided particulate material form a membrane due to particle to particle cohesion of evenly distributed, closely associated particles.

The low boiling organic liquids useful in the present invention are preferably water-miscible and contain from 1 to 6 carbon atoms. The term "low boiling" as used herein shall mean organic liquids which have a boiling point generally no more than 100° C. These liquids enable the particulate solids to remain in finely divided form without significant agglomeration. Such low boiling organic liquids are exemplified by: alcohols such as methanol, ethanol, propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is the preferred low boiling organic liquid.

Low boiling organic liquids may be employed in applying the particles to form the membranes of this invention. Typically, the liquids are used in an amount sufficient to form a dispersion of the particulate material. The amount of liquid is typically up to about 30 volume percent of the dispersion, preferably from about 3 up to about 5 volume percent, and most preferably from about 3.5 to about 4.5 volume percent. The particulate material is preferably added to a low boiling organic liquid to form a slurry and then this slurry is diluted with water to form an aqueous dispersion. The resulting slurry retains the particles in finely divided form wherein most of the particles are dispersed to a particle size of less than about 10 microns.

This invention also provides methods for pest control and enhanced horticultural effects by forming said membrane on the surface of the horticultural substrate. The foregoing discussions regarding i) said membrane being comprised of one or more layers of particulate material, ii) said particulate material being finely divided, iii) said membrane allowing for the transpiration of water vapor from said substrate through said membrane, and iv) application techniques for applying said layers to the horticultural substrate, as well as the specific embodiments discussed herein, also apply to these methods.

The pests controlled by this invention refer to arthropods including insects, mites, spiders and related animals and diseases of various pathogens such as fungi, bacteria and virus. Diseases can be transmitted in a number of ways such as wind currents, water splash and/or arthropod transmission. Examples of diseases commonly caused by wind currents and water splash include: Fire blight (bacteria—*Erwinia amylovora*), apple scab (fungus—*Venturia inaequalis*), Potato Blight (fungus—*Phytophthora infestans*), Soft rots (fungus—*Botrytis cinerea*), Leaf blight and leaf spot (bacteria—Xanthomonas sp.), and bacterial leaf spot and leaf blight (bacteria—Pseudomonas sp.). Examples of diseases commonly caused by arthropod transmission are the fungus disease, Dutch Elm disease, of American Elm by the European elm beetle; the bacterial disease, Fire blight, of apples and pears by flies, beetles and other insects; the virus disease, Curly Top, of sugar beets by the beet leaf hopper. Disease control also applies to those secondary infections of wound sites on a plant that results from arthropod feeding such as brown rot infection of stone fruits that results when the disease organism enters the plant through plum curculio feeding sites.

This invention can also provide the benefit of enhanced horticultural effects including improved color, smoother fruit surface, increased soluble solids, e.g., sugars, acidity, etc., reduced bark and fruit cracking, reduced plant temperature and reduced russetting.

The following examples are illustrative of embodiments of the invention and are not intended to limit the invention as encompassed by the claims forming part of the application.

EXAMPLE 1

This example demonstrates that coating a plant substrate with a membrane of finely divided particles greatly reduces the degree of infection as compared to a substrate not coated with a particulate membrane. Efficacy of various particulate membranes toward disease control was demonstrated by screening evaluations of *Botrytis cinerea* on strawberry petals (*Fragaria x ananassa Pucheene*). All preparations in Tables III and IV were made by applying suspensions of the particles listed in the table prepared by first dispersing 5 grams of the identified particle in 10 ml methanol which is then brought to 100 ml with deionized water. Petals were then sprayed with this suspension using a Paasche air brush to run off. The petals were allowed to air dry and then 10 μl of *Botrytis inoculum* (3.6×10$^7$ spores/ml) was added over the petals. The petals were then incubated in a 100% humidity chamber for 24 hours.

TABLE III

Fungus Efficacy of surface treated and untreated particles

| Particle | % Infection after 24 hrs | Advancing Contact Angle (°) | Receding Contact Angle (°) |
|---|---|---|---|
| Control - no particles | 88.9 | — | — |
| Methanol | 76.5 | — | — |
| Kaolin hydrous [ST][1] | 73.0 | 155.5 | 0 |
| Kaolin calcined[2] | 68.0 | 19.4 | 20.5 |
| Kaolin hydrous[3] | 63.8 | 29 | 30.1 |
| Kaolin calcined [ST][4] | 62.0 | 166 | 102 |
| Calcium Carbonate[5] | 57.0 | 28.4 | 32.5 |
| Talc[6] | 49.3 | 180 | 12.8 |
| Calcined Kaolin [ST][7] | 44.7 | 146 | 128 |
| Calcium Carbonate [ST][8] | 36.8 | 180 | 171 |
| Translink ® 77 | 23.6 | 153 | 120 |

[1] ASP ® 900 (Engelhard Corporation) treated with stearate [2] Satintone ® W (Engelhard Corporation) [3] ASP ® 900 (Engelhard Corporation) [4] Satintone ® W (Engelhard Corporation) treated with stearate [5] Atomite ® (ECC Int.) [6] Vantalc ® 6H (RT Vanderbilt) [7] Translink ® 37 (Engelhard Corporation) [8] Kotamite ® (ECC Int.) Data are the mean of 3 independent replications, each containing 10 strawberry petals.

Infection was measured by the presence of a necrotic lesion characteristic of a Botrytis infection. The data was analyzed by the Duncan's multiple range test (P=0.05) on the arcsine transformed percentages and are presented as untransformed mean for convenience).

EXAMPLE 2

Performing the same evaluations and comparing surface treated particles to untreated particles of calcined kaolin gave the results in Table IV.

TABLE IV

Fungus Efficacy of surface treated calcined kaolin

Figure 1:
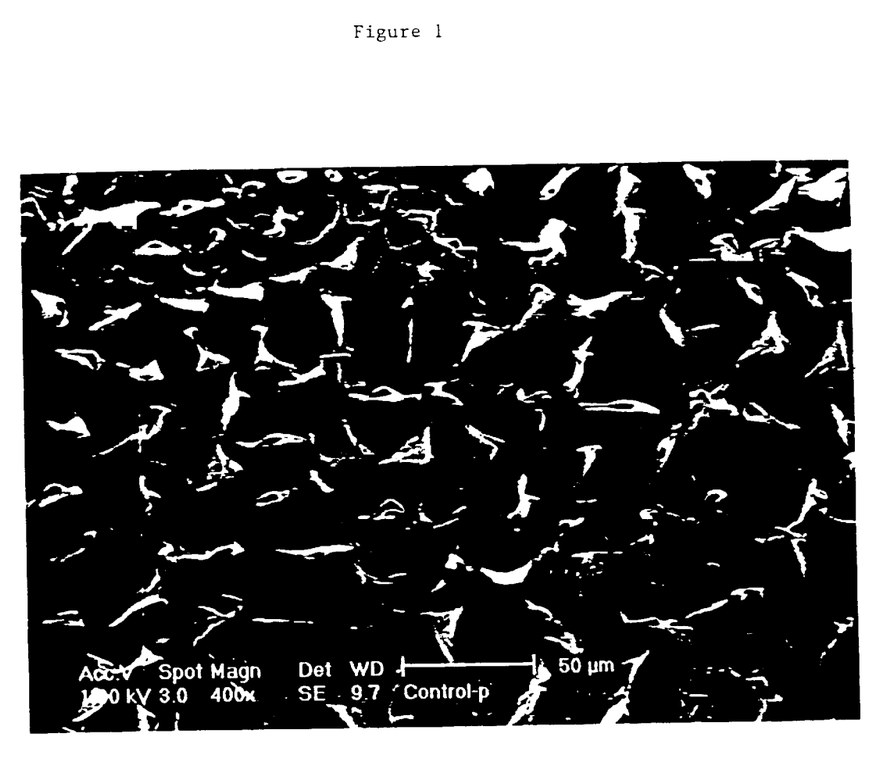
FIG. 1 is a scanning electron micrograph of an untreated petunia petal.
Figure 2:
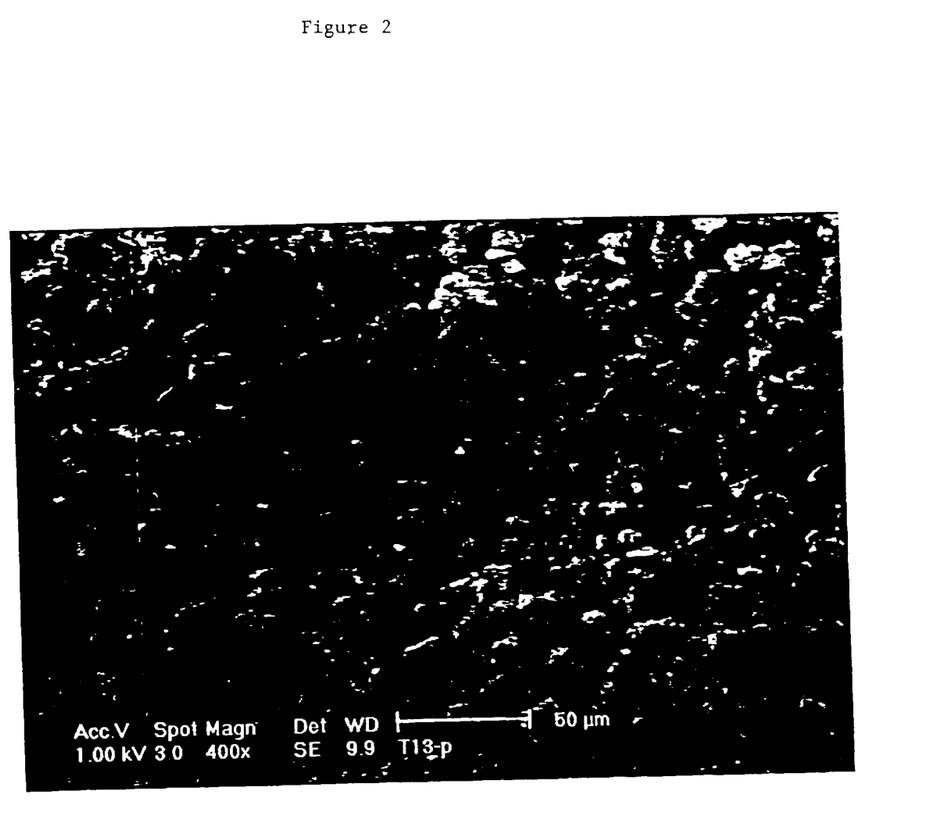
FIG. 2 is a scanning electron micrograph of a petunia petal coated with a membrane of octylsilane treated calcined kaolin particles.
Figure 3:
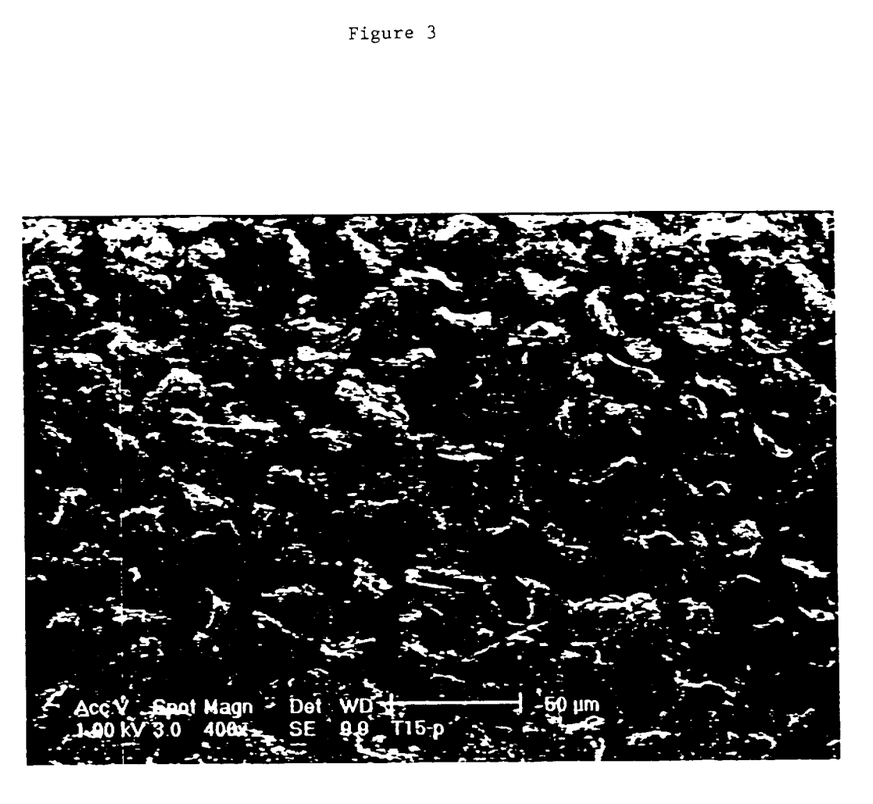
FIG. 3 is a scanning electron micrograph of a petunia petal coated with a membrane of vinyl silane calcined kaolin particles.
Figure 4:
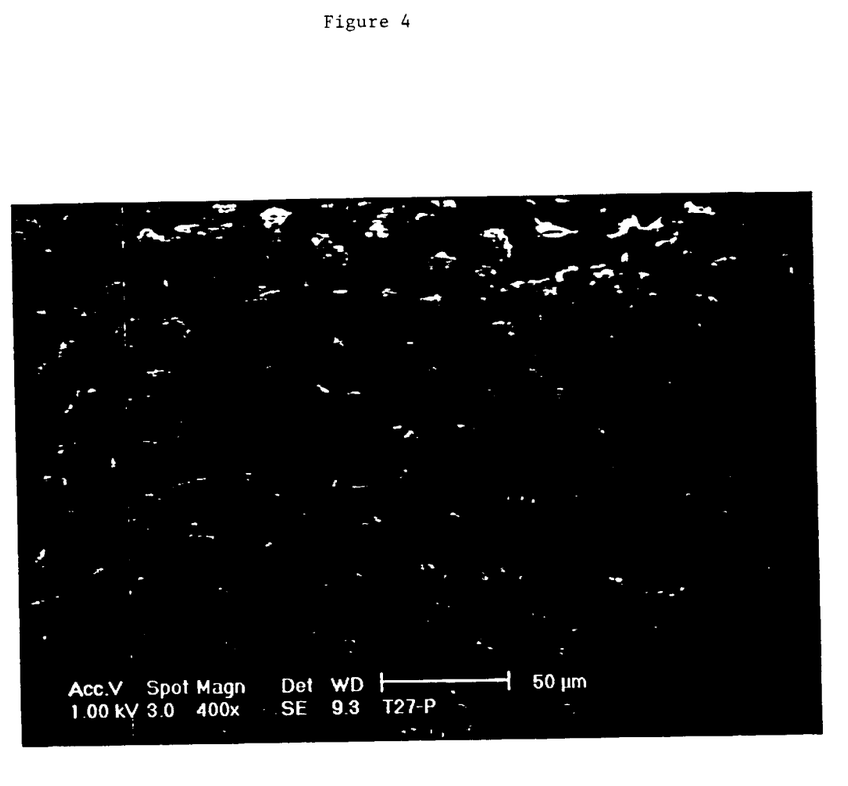
FIG. 4 is a scanning electron micrograph of a petunia petal coated with a membrane of methylethoxysiloxane treated calcined kaolin particles.
Figure 5:
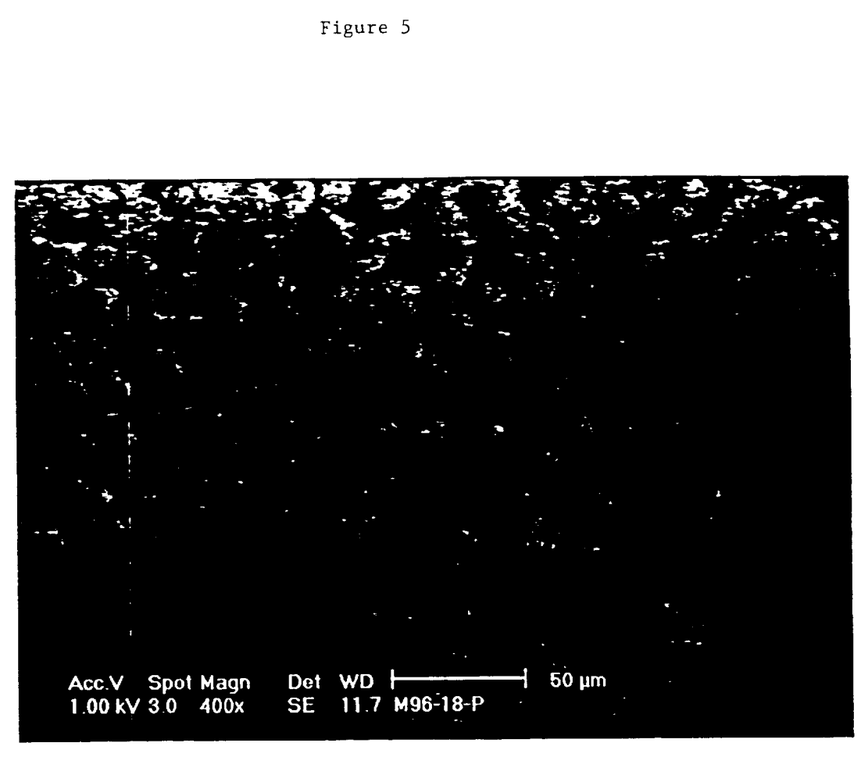
FIG. 5 is a scanning electron micrograph of a petunia petal coated with a membrane of a calcined kaolin treated with a siloxane material.
Figure 6:
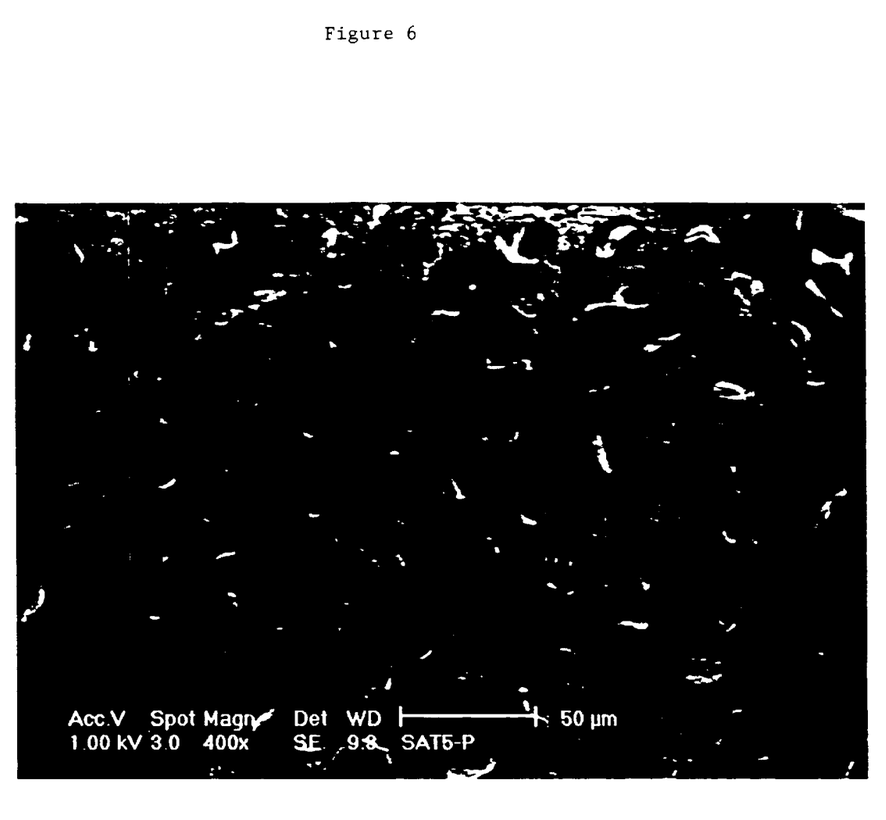
FIG. 6 is a scanning electron micrograph of a petunia petal coated with a membrane of a calcined kaolin.

| Particles | % Infection after 24 hrs | Advancing Contact Angle (°) | Receding Contact Angle (°) | Character of particle coating |
|---|---|---|---|---|
| Control - no particles | 88 | — | — | FIG. 1 |
| octylsilane treated[1] Satintone ® W | 25 | 180 | 180 | FIG. 2 |
| vinylsilane treated[2] Satintone ® W | 29 | 164 | 140 | FIG. 3 |
| methylethoxysiloxane treated[3] Satintone ® W | 25 | 180 | 154 | FIG. 4 |
| Translink ® 77 | 0 | 153 | 120 | FIG. 5 |
| Satintone ® W | — | — | — | FIG. 6 |

[1]1% A-137 (Witco) [2]1% A-151 (Witco) [3]1% A-272 (Witco)

Scanning electron micrographs shown in FIGS. 1–6 were collected with a Philips XL 30 FEG scanning electron microscope (SEM) at 1 Kv accelerating voltage and 1×10 (−5) mbar vacuum. Samples of petunia petals were coated with particle membranes as described in Example 1 and placed in the instrument without any additional sample preparation. The vacuum caused a collapse of the surface irregularities of the petal substrate, but did not affect the particle membranes as illustrated in FIGS. 2–6. All images are presented at 400×magnification.

FIG. 1 illustrates the uneven surface of an uncoated petunia petal. Under an ordinary optical go microscope one observes a surface containing many peaks and valleys. These peaks are collapsed under the conditions necessary to collect the SEM image. Ordinary optical images, however, often do not show the membrane surface because the membranes are very thin and transparent to visible light. SEM techniques, however, can capture an image of the surface of such membranes.

FIGS. 2–4 illustrate the membrane surface prepared from calcined kaolin particles (1.2 micron median particle size) treated with the various hydrophobic wetting agents listed in Table IV.

FIG. 5 illustrates the surface of the membrane prepared from Translink® 77 which has fewer and smaller voids than those voids appearing in FIGS. 2–4.

FIG. 6 illustrates the surface of the membrane prepared from the same calcined kaolin particles (0.8 micron medium particle size) used in the manufacture of Translink® 77. The image clearly shows regularly spaced large voids on the order of 20 microns diameter.

EXAMPLE 3

"Seckel" pear trees received the following treatments: 1) conventional pesticide applications applied according to the presence of economic levels of pests using the Virginia, West Virginia and Maryland Cooperative Extension 1997 Spray Bulletin for Commercial tree Fruit Growers publication 456-419, 2) no treatment, 3) weekly application of Translink® 77 beginning in Apr. 29, 1997, 4) weekly application of calcined kaolin (Satintone® 5HP). beginning in Apr. 29, 1997, 5) weekly application of treated calcium carbonate (SuperCoat®—commercially available from English China Clay) beginning in Apr. 29, 1997. 6) weekly application of Translink 37® beginning in Apr. 29, 1997. Treatments (3), (5) and (6) applied 25 pounds material suspended in 4 gal methanol and added to 100 gal water. Treatment (4) applied 25 pounds material suspended in 100 gal water with the addition of 27 oz Ninex® MT-603 and 2 pints Toximul. These treatments were applied at the rate of 125 gal/acre using an orchard sprayer. This mixture was applied at the rate of 125 gal/acre using an orchard sprayer. Treatments ended Sep. 15, 1997. The treatments were arranged in a randomized complete block design with 2 replications and 4 trees/plot. A freeze of 25° F. occurred on Oct. 23, 1997 and freeze damage of foliage was evaluated on Oct. 28, 1997. Freeze damage was evaluated by collecting 40 leaves/plot (10 from each tree). Leaves with necrosis on the leaf margin to the midvein that extended to the abaxial side of the leaf exhibited freeze damage. Undamaged leaves lacked this necrosis. Each leaf was categorized as damaged or undamaged and percentage undamaged from each plot calculated. Data were analyzed using Analysis of variance using a randomized complete block design.

TABLE V

| Treatment | Undamaged leaves (%) |
|---|---|
| Conventional | 2.5 |
| Control | 2.5 |
| Translink 77 | 81.5 |
| Satintone 5HP | 11.5 |
| Supercoat | 67.0 |
| Translink 37 | 69.0 |

These data demonstrate that freeze damage was extensive when no particles were applied (conventional and control, 2.5% each). Freeze damage was extensive when a hydrophilic particle was applied to the tree (Satintone 5HP, 11.5%). Freeze damage was moderated when hydrophobic particles were applied to the trees (Translink 77, Supercoat, and Translink 37, 81.5%, 67%, and 69%, respectively). These data demonstrate that the presence of a hydrophobic particle membrane will moderate freeze damage.

EXAMPLE 4

"Red Delicious" apple trees received the following treatments: 1) Conventional pesticide applications applied according to the presence of economic levels of pests using the Virginia, West Virginia and Maryland Cooperative Extension 1997 Spray Bulletin for Commercial tree Fruit Growers publication 456-419, 2) no treatment, 3) weekly application of Translink® 77 beginning in Mar. 11, 1997, 4) weekly application of calcined kaolin (Satintone® 5HP) beginning in Apr. 29, 1997, and 5) weekly application of treated calcium carbonate (SuperCoat®—commercially available from English China Clay) beginning in Apr. 29, 1997. Treatments (3), and (5) applied 25 pounds material suspended in 4 gal methanol and added to 100 gal water. Treatment (4) applied 25 pounds material suspended in 100 gal water with the addition of 27 oz Ninex® MT-603 and 2 pints Toximul. These treatments were applied at the rate of 125 gal/acre using an orchard sprayer. This mixture was applied at the rate of 125 gal/acre using an orchard sprayer. The treatments were arranged in a randomized complete block design with 4 replications and 3 trees/plot. Treatments were not irrigated and received 21.58 cm of precipitation from May 1 to Aug. 30, 1997. Fruit were harvested at maturity; fruit number were measured at harvest. Data were analyzed using Analysis of variance using a randomized complete block design.

TABLE VI

| Treatment | Fruit number/tree |
| --- | --- |
| Conventional | 322 |
| Control | 246 |
| Translink 77 applied 3/11/97 | 382 |
| Satintone 5HB applied 4/29/97 | 302 |
| Supercoat applied 4/29/97 | 301 |

The weekly application of Translink® 77 before bud break and the occurrence of a severe frost on Apr. 9, 1997 with a minimum temperature of 20° F., moderated the frost damage as demonstrated by a larger number of fruit (382) reaching maturity compared to Satintone® HB (302) or Supercoat® (301). The weekly application of Translink® 77 before bud break also moderated the frost damage to fruit compared to the conventional treatment and the untreated control (322 and 246 respectively), neither of, which received any pesticide applications prior to the frost. The application after the frost of Supercoat®, a hydrophobic particle, or Satintone® 5HB, a hydrophilic particle, did not increase the number of fruit/tree.

EXAMPLE 5

"Golden Delicious" apples received 3 treatments: 1) commercial pesticide application applied according to the presence of economic levels of pests using the Virginia, West Virginia and Maryland Cooperative Extension 1997 Spray Bulletin for Commercial tree Fruit Growers publication 456-419, 2) full rate of Translink® 77, and 3) half rate of Translink® 77. Treatments (2) and (3) applied 25 and 12.5 pounds material, respectively, suspended in 4 and 2 gal methanol, respectively, and added to 100 gal water. This mixture was applied at the rate of 200 gal/acre using an orchard sprayer. The treated area was approximately 1 acre plots with 2 replications of each treatment in a randomized block design. At harvest the plots were commercially harvested and processed by a commercial grading line. At the time of grading, 100 fruit from each plot were randomly chosen to determine surface defects. The data are reported in Table VII.

TABLE VII

| Treatment | Russetting downgrade (%) |
| --- | --- |
| Translink ® 77 full rate | 3.3 |
| Translink ® 77 half rate | 3.9 |
| Conventional | 13.8 |

Application of Translink® 77 at the full and half rate reduced russetting on the apple surface compared to the conventional treatment.

EXAMPLE 6

"Stayman" apples received 2 treatments: 1) commercial pesticide application applied according to the presence of economic levels of pests using the Virginia, West Virginia and Maryland Cooperative Extension 1997 Spray Bulletin for Commercial tree Fruit Growers publication 456-419, 2) Translink® 77 treatment applied 25 pounds material suspended in 4 gal methanol and added to 96 gal water. This mixture was applied at the rate of 200 gal/acre using an orchard sprayer. Each treatment was applied to 1 acre blocks with no randomization. Apples were harvested commercially and processed on a commercial grading line. Data presented represent percent packout from the commercial grading line. At time of grading 100 fruit each treatment were randomly chosen to evaluate for surface defects. Cracking percentage was the percentage of fruit with visible cracks in the fruit. The data are reported in Table VIII.

TABLE VIII

| Treatment | Fruit cracking (%) |
| --- | --- |
| Translink ® 77 | 2 |
| Conventional | 22 |

The application of Translink® 77 deceased the cracking of apple fruit compared to the conventional treatment.

What is claimed is:

1. A coated substrate comprising a horticultural substrate selected from the group consisting of fruits, vegetables, trees, flowers, grasses, roots, and landscape and ornamental plants wherein the surface of said substrate is coated with a membrane formed from a slurry comprising water and one or more particulate materials, the membrane comprised of one or more particulate layers, said layers comprising one or more particulate materials selected from the group consisting of calcium carbonate, hydrous kaolin, calcined kaolin and mixtures thereof, said particulate materials being finely divided, and wherein said membrane allows for the exchange of gases on the surface of said substrate and the particulate material comprises a hydrophilic core and a hydrophobic outer surface.

2. The coated substrate of claim 1 wherein said particulate materials are hydrophobic.

3. The coated substrate of claim 1 wherein said particulate material has a Receding Contact Angle of greater than 90°.

4. The coated substrate of claim 1 wherein the particulate material has a particle size distribution wherein up to 90% of the particles have a particle size of under about 10 microns.

5. The coated substrate of claim 1, wherein the particulate materials comprise one of calcium carbonate and hydrous kaolin, hydrous kaolin and calcined kaolin, calcium carbonate and calcined kaolin.

6. The coated substrate of claim 1 wherein said hydrophobic outer surface materials are selected from the group consisting of chrome complexes, organic titanates, organic zirconate or aluminate coupling agents, organofunctional silanes, modified silicone fluids and fatty acids and salts thereof.

7. The coated substrate of claim 1 wherein the substrate is selected from the group consisting of agricultural and ornamental crops.

8. The coated substrate of claim 1 wherein the substrate is selected from the group consisting of fruits, vegetables, trees, flowers, grasses, seeds, roots, and landscape and ornamental plants.

9. The coated substrate of claim 1 wherein the finely divided particulate materials have a median individual particle size below about 3 microns.

10. The coated substrate of claim 1 wherein the hydrophilic core particulate materials are selected from the group consisting of calcium carbonate, calcined kaolin and mixtures thereof.

11. A coated substrate comprising a horticultural substrate selected from the group consisting of fruits, vegetables, trees, flowers, grasses, seeds, roots, and landscape and ornamental plants wherein the surface of said substrate is coated with a membrane comprised of one or more particulate layers, said layers comprising one or more hydrophobic particulate materials, said hydrophobic particulate materials comprising i) a hydrophilic core selected from the group consisting of calcium carbonate, calcined kaolin and mixtures thereof and i) a hydrophobic outer surface, said particulate materials have a median individual particle size of about one micron or less, and wherein said membrane allows for the exchange of gases on the surface of said substrate.

12. A method for pest control on horticultural substrates selected from the group consisting of fruits, vegetables, trees, flowers, grasses, roots, and landscape and ornamental plants which comprises applying a slurry comprising water and one or more particulate materials, selected from the group consisting of calcium carbonate, hydrous kaolin, calcined kaolin and mixtures thereof, to the surface of said substrate to form a membrane comprised of one or more particulate layers, said layers comprising the particulate materials, said particulate materials being finely divided, and wherein said membrane allows for the exchange of gases on the surface of said substrate and the membrane is hydrophobic.

13. The method of claim 12 wherein said particulate material has a Receding Contact Angle of greater than 90°.

14. The method of claim 12 wherein the particulate material has a particle size distribution wherein up to 90% of the particles have a particle size of under about 10 microns.

15. The method of claim 12, wherein the particulate materials comprise one of calcium carbonate and hydrous kaolin, hydrous kaolin and calcined kaolin, calcium carbonate and calcined kaolin.

16. The method of claim 12 wherein the substrate is selected from the group consisting of agricultural and ornamental crops.

17. The method of claim 12 wherein the substrate is selected from the group consisting of fruits, vegetables, trees, flowers, grasses, seeds, roots, and landscape and ornamental plants.

18. The method of claim 12 wherein the finely divided particulate materials have a median individual particle size below about 3 microns.

19. The method of claim 12 wherein the particulate material comprises a hydrophilic core and a hydrophobic outer surface.

20. The method of claim 19 wherein said hydrophobic outer surface materials are selected from the group consisting of chrome complexes, organic titanates, organic zirconate or aluminate coupling agents, organofunctional silanes, modified silicone fluids and fatty acids and salts thereof.

21. The method of claim 19 wherein the hydrophilic core particulate materials are selected from the group consisting of calcium carbonate, calcined kaolin and mixtures thereof.

22. A method for pest control on horticultural substrates selected from the group consisting of fruits, vegetables., trees, flowers, grasses, seeds, roots, and landscape and ornamental plants, which comprises forming on the surface of said substrate a membrane comprised of one or more particulate layers, said layers comprising one or more hydrophobic particulate materials, said hydrophobic particulate materials comprising i) a hydrophilic core selected from the group consisting of calcium carbonate, calcined kaolin and mixtures thereof, and ii) a hydrophobic outer surface, said particulate materials have a median individual particle size of about one micron or less, and wherein said membrane allows for the exchange of gases on the surface of said substrate.

23. A method for enhancing the horticultural effect of horticultural substrates selected from the group consisting of fruits, vegetables, trees, flowers, grasses, roots, and landscape and ornamental plants which comprises applying a slurry comprising water, a surfactant, and one or more particulate materials, selected from the group consisting of calcium carbonate, hydrous kaolin, calcined kaolin and mixtures thereof, to the surface of said substrate to form a membrane comprised of one or more particulate layers and the surfactant, said layers comprising one or more particulate materials, said particulate materials being finely divided, and wherein said membrane allows for the exchange of gases on the surface of said substrate.

24. The method of claim 23 wherein said particulate materials are hydrophobic.

25. The method of claim 23 wherein said particulate material has a Receding Contact Angle of greater than 90°.

26. The method of claim 23 wherein the particulate material has a particle size distribution wherein up to 90% of the particles have a particle size of under about 10 microns.

27. The method of claim 23, wherein the particulate materials comprise one of calcium carbonate and hydrous kaolin, hydrous kaolin and calcined kaolin, calcium carbonate and calcined kaolin.

28. The method of claim 23 wherein the substrate is selected from the group consisting of agricultural and ornamental crops.

29. The method of claim 23 wherein the substrate is selected from the group consisting of fruits, vegetables, trees, flowers, grasses, seeds, roots, and landscape and ornamental plants.

30. The method of claim 23 wherein the finely divided particulate materials have a median individual particle size below about 3 microns.

31. The method of claim 23 wherein the particulate material comprises a hydrophilic core and a hydrophobic outer surface.

32. The method of claim 31 wherein said hydrophobic outer surface materials are selected from the group consisting of chrome complexes, organic titanates, organic zirconate or aluminate coupling agents, organofunctional silanes, modified silicone fluids and fatty acids and salts thereof.

33. The method of claim 31 wherein the hydrophilic core particulate materials are selected from the group consisting of calcium carbonate, calcined kaolin and mixtures thereof.

34. A method for enhancing the horticultural effect of horticultural substrates selected from the group consisting of fruits, vegetables, trees, flowers, grasses, seeds, roots, and landscape and ornamental plants, which comprises forming on the surface of said substrate a membrane comprised of one or more particulate layers, said layers comprising one or more hydrophobic particulate materials, said hydrophobic particulate materials comprising i) a hydrophilic core selected from the group consisting of calcium carbonate, calcined kaolin and mixtures thereof, and ii) a hydrophobic outer surface, said particulate materials have a median individual particle size of about one micron or less, and wherein said membrane allows for the exchange of gases on the surface of said substrate.

35. A coated substrate comprising a horticultural substrate selected from the group consisting of fruits, vegetables, trees, flowers, grasses, roots, and landscape and ornamental plants wherein the surface of said substrate is coated with a membrane comprised of one or more particulate layers, said layers comprising one or more particulate materials, said particulate materials selected from the group consisting of calcium carbonate, calcined kaolin, hydrophobic treated hydrous kaolin, hydrophobic treated talc, mica, attapulgite, pyrophyllite, wollastonite, feldspar, sand, quartz, diatomaceous earth, baryte, ceramic, glass and organic microspheres, aluminum trihydrate, ceramic fibers, glass fibers, colorants, titanium dioxide, and mixtures thereof and being finely divided and hydrophobic, and wherein said membrane contains gaps that do not exceed about 5 µm and the membrane allows for the exchange of gases on the surface of said substrate and the membrane is hydrophobic.

36. A coated substrate comprising a horticultural substrate selected from the group consisting of fruits, vegetables, trees, flowers, grasses, roots, and landscape and ornamental plants wherein the surface of said substrate is coated with a membrane comprised of one or more particulate layers, said layers comprising one or more particulate materials, said particulate materials comprising hydrous kaolin and being finely divided wherein the particulate materials have a mean individual particle size below about 10 microns, and wherein said membrane allows for the exchange of gases on the surface of said substrate and the particulate materials further comprise calcium carbonate, calcined kaolin, or calcium carbonate and calcined kaolin.

37. The coated substrate of claim 36, wherein the particulate materials have a mean individual particle size below about 1 micron.

38. A method for disease control on horticultural substrates selected from the group consisting of fruits, vegetables, trees, flowers, grasses, roots, and landscape and ornamental plants which comprises applying a slurry comprising water, a surfactant, and one or more particulate materials to the surface of said substrate to form a membrane comprised of one or more particulate layers and the surfactant, said layers comprising one or more particulate materials selected from the group consisting of calcium carbonate, calcined kaolin, hydrophobic treated hydrous kaolin, hydrophobic treated talc, mica, attapulgite, pyrophyllite, wollastonite, feldspar, sand, quartz, diatomaceous earth, baryte, ceramic, glass and organic microspheres, aluminum trihydrate, ceramic fibers, glass fibers, colorants, titanium dioxide, and mixtures thereof, said particulate materials being finely divided and hydrophobic, and wherein said membrane allows for the exchange of gases on the surface of said substrate.

39. The method of claim 38, wherein the particulate materials have a mean individual particle size below about 1 micron.

* * * * *